US009615961B2

(12) United States Patent
Johansson et al.

(10) Patent No.: US 9,615,961 B2
(45) Date of Patent: Apr. 11, 2017

(54) PERCUTANEOUS IMPLANT AND OSTOMY METHOD

(75) Inventors: Martin Johansson, Valda (SE); Robert Axelsson, Gränna (SE); Jan Erik Axelsson, Örebro (SE)

(73) Assignee: Ostomycure AS, Oslo (NO)

( * ) Notice: Subject to any disclaimer, the term of this patent is extended or adjusted under 35 U.S.C. 154(b) by 76 days.

(21) Appl. No.: 14/006,647

(22) PCT Filed: Mar. 26, 2012

(86) PCT No.: PCT/GB2012/050668
§ 371 (c)(1),
(2), (4) Date: Nov. 8, 2013

(87) PCT Pub. No.: WO2012/131351
PCT Pub. Date: Oct. 4, 2012

(65) Prior Publication Data
US 2014/0052085 A1 Feb. 20, 2014

(30) Foreign Application Priority Data
Mar. 25, 2011 (GB) .................................. 1105126.5

(51) Int. Cl.
*A61F 5/445* (2006.01)
(52) U.S. Cl.
CPC ...... *A61F 5/445* (2013.01); *A61F 2005/4455* (2013.01)
(58) Field of Classification Search
USPC ....................................................... 604/338
See application file for complete search history.

(56) References Cited

U.S. PATENT DOCUMENTS

| 3,663,965 A | 5/1972 | Lee, Jr. et al. |
| 4,119,100 A | 10/1978 | Rickett |

(Continued)

FOREIGN PATENT DOCUMENTS

| EP | 0477475 B1 | 4/1992 |
| EP | 1632201 B1 | 3/2006 |

(Continued)

OTHER PUBLICATIONS

International Search Report and Written Opinion, PCT/GB2012/050668, mailed Sep. 28, 2012.

(Continued)

*Primary Examiner* — Tatyana Zalukaeva
*Assistant Examiner* — Guy K Townsend
(74) *Attorney, Agent, or Firm* — Winston & Strawn LLP

(57) ABSTRACT

A percutaneous ostomy implant for implantation into the abdominal wall of a patient is provided, which includes a connecting member for mounting an external detachable device thereto; a first tubular ingrowth member depending from the connecting member; and a second tubular ingrowth member depending from the connecting member and being radially outwardly spaced from the first tubular ingrowth member. The first tubular ingrowth member is configured and dimensioned to receive a bowel segment within it to allow the stoma and serosal tissue of that bowel segment to infiltrate the first tubular ingrowth member. The second tubular member is configured and dimensioned to abut dermal tissue to allow the dermal tissue to infiltrate the second tubular ingrowth member, thereby securing and sealing the ostomy implant to the dermis.

20 Claims, 7 Drawing Sheets

(56) References Cited

U.S. PATENT DOCUMENTS

| | | | | |
|---|---|---|---|---|
| 4,183,357 | A | 1/1980 | Bentley et al. | |
| 4,217,664 | A | 8/1980 | Faso | |
| 5,098,397 | A * | 3/1992 | Svensson | A61M 39/0247 604/174 |
| 5,269,774 | A | 12/1993 | Gray | |
| 5,423,761 | A | 6/1995 | Hein et al. | |
| 5,425,761 | A | 6/1995 | Lundgren | |
| 5,882,341 | A | 3/1999 | Bousquet | |
| 6,017,355 | A | 1/2000 | Hessel et al. | |
| 6,438,397 | B1 | 8/2002 | Bosquet et al. | |
| 7,699,824 | B2 * | 4/2010 | Axelsson | A61F 5/4407 604/317 |
| 7,935,096 | B2 * | 5/2011 | Johansson | A61M 25/02 604/175 |
| 8,647,304 | B2 * | 2/2014 | Axelsson | A61F 5/445 604/164.04 |
| 8,821,462 | B2 * | 9/2014 | Axelsson | A61F 5/445 604/332 |
| 8,852,217 | B2 * | 10/2014 | Woodruff | A61M 5/14276 600/37 |
| 2001/0051794 | A1 | 12/2001 | Bestetti et al. | |
| 2002/0099344 | A1 | 7/2002 | Hessel et al. | |
| 2004/0006396 | A1 | 1/2004 | Ricci et al. | |
| 2006/0052759 | A1 | 3/2006 | Johansson et al. | |
| 2007/0244452 | A1 * | 10/2007 | Axelsson | A61F 5/448 604/338 |
| 2009/0192464 | A1 | 7/2009 | Axelsson et al. | |
| 2010/0174255 | A1 * | 7/2010 | Axelsson | A61F 5/448 604/333 |
| 2011/0178540 | A1 | 7/2011 | Axelsson et al. | |
| 2011/0196324 | A1 * | 8/2011 | Johansson | A61M 25/02 604/338 |
| 2012/0123361 | A1 | 5/2012 | Johansson et al. | |
| 2012/0289916 | A1 * | 11/2012 | Johansson | A61M 25/02 604/337 |
| 2014/0052085 | A1 * | 2/2014 | Johansson | A61F 5/445 604/338 |

FOREIGN PATENT DOCUMENTS

| | | |
|---|---|---|
| EP | 1825839 A1 | 8/2007 |
| EP | 2027835 A1 | 2/2009 |
| GB | 2045084 | 10/1980 |
| GB | 2105197 | 3/1983 |
| JP | 2002507901 | 3/2002 |
| RU | 2 124 335 C1 | 1/1999 |
| WO | 94/18919 A1 | 9/1994 |
| WO | WO9858691 A1 | 12/1998 |
| WO | WO0062722 A1 | 10/2000 |
| WO | WO0108597 A1 | 2/2001 |
| WO | WO2005056079 A1 | 6/2005 |
| WO | WO2007099500 A1 | 9/2007 |
| WO | WO2009024568 A1 | 2/2009 |
| WO | WO2010000851 A2 | 1/2010 |
| WO | WO2010125346 A1 | 11/2010 |

OTHER PUBLICATIONS

International Search Report and Written Opinion, Appl. No. PCT/IB2007/050646, Jul. 27, 2007.
U.S. Appl. No. 12/280,610 Restriction Requirement, Dec. 23, 2010.
U.S. Appl. No. 12/280,610, Non-Final Office Action, Mar. 22, 2011.
U.S. Appl. No. 12/280,610, Applicant-Initiated Interview Summary, Sep. 16, 2011.
U.S. Appl. No. 12/280,610, Non-Final Office Action, Mar. 16, 2012.
U.S. Appl. No. 12/280,610, Final Office Action, Jan. 9, 2013.
U.S. Appl. No. 12/280,610, Advisory Action, Mar. 15, 2013.
U.S. Appl. No. 12/280,610, Applicant-Initiated Interview Summary, Apr. 12, 2013.
European Search Report, Application No. 07114671 dated Dec. 4, 2007.
International Search Report, PCT/EP2003/060837, mailed Nov. 7, 2008.
British Search Report, GB1105126.5, mailed Jul. 15, 2011.
British Search Report, GB1105126.5, mailed Jan. 20, 2012.
Decision of Grant, Appl. No. RU 2013147630, Jul. 1, 2016.

* cited by examiner

PERCUTANEOUS IMPLANT AND OSTOMY METHOD

This application is a 371 filing of International Patent Application PCT/GB2012/050668 filed Mar. 26, 2012, which claims priority to British application no. 1105126.5 filed Mar. 25, 2011.

BACKGROUND

The present invention relates to a percutaneous ostomy implant and a surgical method, which may use that implant, preferably for creating a continent reservoir in communication with a percutaneous port.

Ileostomy and colostomy are common operations which may be necessitated, for example, by malignancy or chronic bowel inflammation. The surgery is called an ileostomy if the colon and rectum are removed and a colostomy if the rectum alone is removed. Similarly an abdominal urostomy is created when the urinary bladder has to be removed due to, for example, bladder cancer. In these operations, a stoma is formed in the abdominal wall to which a bowel segment is connected. Ostomy is a generic term for any such procedure where a stoma is created.

The stoma in most cases has to be connected to a bag to collect bodily waste. However, instead of a conventional ileostomy, it is possible to make a reservoir known as a "Kock pouch" from the distal part of the ileum. It is formed in such a way that a nipple valve is created which serves to close the reservoir, whilst allowing it to be drained intermittently by means of a catheter. This is an example of a so-called continent ileostomy (CI); it was formerly an attractive alternative to conventional ileostomy, but is now rarely used. The complexity of the procedure and the high potential for complications—most of them related to dysfunction of the continence nipple valve—has deterred many surgeons from adopting the operation today.

The ileopouch anal anastomosis (IPAA) is today the gold standard worldwide for these patients, but as with a CI, this operation is also risky and failures are common, mostly leading to pouch excision with loss of bowel. Conversion of a failed IPAA to a CI would be a preferable option but again, surgeons are again reluctant to perform this complex and unreliable technique. Likewise, conversion of a malfunctional orthotopic neobladder or Bricker urostomy would be desirable.

In their earlier patent application EP 1632201-A1, the present applicants disclosed a percutaneous ostomy implant comprising a solid-walled cylindrical body and an anchoring section in the form of a circular flange. The device was designed to be implanted through the abdominal wall and secured by an anchoring section located below the muscle layer. This section comprised inner and outer concentric rings interconnected by S-shaped members in order to provide an axially resilient structure which could absorb shear stresses and consequently reduce the risk of tissue damage. Spaces around the S-shaped members and the provision of numerous apertures in the rings allowed for tissue ingrowth and vascularization. It was proposed to connect the device to the side of the bowel wall and by providing a removable lid on the cylindrical body a continent ostomy could be provided.

A development of this implant was disclosed in WO 2007/099500 in which the solid-walled cylindrical body was replaced by an axially outer tubular part spaced from the anchoring section by circumferentially-spaced legs. The tubular part penetrated the skin and formed a ring for connection to a bag or lid. This implant was designed to receive a bowel section drawn up through it; the spaces between the legs allowed the generation of a tissue bond between the inner part of the abdominal wall and the serosal tissue of the bowel in order to provide a more secure, stable, leak-proof and well-vascularized tissue-implant junction. In some embodiments, a circumferential ingrowth mesh was additionally provided. This extended along most of the length of the tubular part with an annular gap being provided between it and the tubular part to facilitate growth of serosal tissue through the mesh.

In a further development, in WO 2009/024568 the present applicants proposed a cylindrical body formed of two axially-spaced tubular parts. The outer tubular part penetrated the skin and provided a connecting ring. The inner tubular part was attached to an anchoring flange of the type previously described. The two parts were connected together by a "distance means" comprising either radially-spaced legs or a rigid cylindrical ingrowth mesh which allowed for the generation of a tissue bond between the abdominal wall and the bowel. By means of this arrangement, a break was provided in the possible infection path along the implant from the skin.

In a still further development, the applicants disclosed in WO/2010/000851 a percutaneous ostomy implant comprising a cylindrical part for mounting an external detachable device, a cylindrical ingrowth mesh and a circular flange for anchoring the implant. The cylindrical part and circular flange were attached to opposite ends of the ingrowth mesh, with the mesh extending inside the cylindrical part. The implant was configured such that when it is implanted in the abdominal wall of a patient, abdominal tissue including the epidermis meets the ingrowth mesh and is able to attach therethrough directly to serosal tissue of a bowel segment inside the implant. Thus, it was based on the hypothesis that by allowing the epidermis to attach directly to the serosal tissue, bacterial infection (i.e. bacterial attachment to implant surface and subsequent migration) can be prevented.

While this implant has been found to be effective in ensuring sound attachment of the serosal tissue to the abdominal tissue, it has a drawback in that it becomes more difficult to ensure a fluid-tight seal between the exterior parts of the implant and the bowel segment. This is because the implant relies upon the bowel segment extending within the cylindrical part and maintaining secure infiltration of serosal tissue through the mesh inside that part to form a good seal to the implant. If the bowel recedes below the cylindrical part, a leakage path may be formed through the mesh, even if the bowel segment and abdominal wall remain integrated and the implant remains secure and free of infection.

SUMMARY OF THE INVENTION

According to the present invention there is provided a percutaneous ostomy implant for implantation into the abdominal wall of a patient, the implant comprising: a connecting member for mounting an external detachable device thereto; a first (inner) tubular ingrowth member depending from the connecting member; and a second (outer) tubular ingrowth member depending from the connecting member and being radially outwardly spaced from the first tubular ingrowth member; wherein the first tubular ingrowth member is adapted to receive a bowel segment within it to form a stoma and serosal tissue of that bowel segment may infiltrate the first tubular ingrowth member; and the second tubular member is adapted to abut dermal tissue such that the dermal tissue may infiltrate the second tubular ingrowth member, thereby securing and sealing the ostomy implant to the dermis.

By means of the present invention, separate ingrowth means are provided for dermal and serosal tissue. In this way the dermal tissue can be caused to ingrow at a location that ensures good attachment and sealing to the implant and which is independent of the ingrowth means provided for the serosal tissue.

The implant may be used, for example, in an ileostomy, colostomy or urostomy.

The connecting member may be any convenient shape, although it is preferably cylindrical and most preferably a circular-based cylinder so that a round opening is provided for attachment of an external device, such as a bag or lid. (The term "axial" relates to the axis of the connecting member in the last case, or to the corresponding direction in other cases.) Similarly, the term "tubular" refers to an open-ended form which preferably, but not necessarily, has a circular base or cross-section. Typically, the sectional shape of the tubular members is similar to that of the connecting member.

For convenience, the end of the implant to which the detachable device is connected in use, i.e. the axially external end, is referred to herein as the top and the opposite end, i.e. the axially internal end is the bottom. It will be appreciated that these are merely arbitrary labels, but they have been chosen for consistency with the orientation of the implants in the accompanying drawings. The term "external detachable device" refers to a detachable device, such as a lid, bag or evacuation device, that is external to the patient. It is recognized that some such devices may comprise at least a portion that is received within the upper axial end of the implant.

Preferably, there is a radial gap provided between the inner and outer ingrowth members. In this way, an annular space for ingrowth between these members may be provided.

Although various ingrowth materials may be used, the first and/or second tubular ingrowth member(s) preferably comprise mesh. The mesh is most conveniently two-dimensional, though three dimensional structures may be used. Although the implant may be made of any biologically-acceptable material, e.g. plastics, it is preferably formed of commercially pure titanium, preferably ASTM Grade 2 titanium. The mesh is preferably laser cut from such titanium.

The implant may have a surface treatment, such as a grit or a blasted surface and/or an electrochemical treatment to achieve optimum topographical properties, physical and chemical surface characteristics (e.g. surface roughness) etc. It is also possible to apply active surface treatments including specialist surface coatings, e.g. metal/metal-oxide/ceramics, to speed up and/or improve healing, prevent infections, etc. Thus, all or part of the implant may be coated with agents facilitating additional protection against infections, e.g. they may be coated with noble metals or other antibacterial agents, or be coated with other organic or inorganic agents facilitating a closer tissue adaptation and sealing. An example of a suitable coating is hydroxyapatite (a mineral form of calcium apatite and a major component and an essential ingredient of normal bone and teeth).

As in certain of the applicant's prior implants, the first tubular ingrowth member preferably extends in the axial direction within the connecting member so that serosal tissue may infiltrate the first tubular ingrowth member within the connecting member. It may therefore be referred to as the 'serosal ingrowth member'. In order to allow for effective ingrowth within the connecting member, a space is preferably provided between the inside of it and the ingrowth member. This may be achieved by providing a radially-inwardly projecting portion of the connecting member to which the serosal member is attached. Thus, the mesh most preferably is attached to a projecting portion within the connecting member and depends downwardly towards the bottom of the implant. In a most preferred embodiment, the connecting and first tubular members are coaxial cylinders.

The second tubular ingrowth member preferably extends in the axial direction so that at least part of it extends around at least part of the connecting member so that dermal tissue may infiltrate the second tubular ingrowth member around the connecting member. It may therefore be termed the 'dermal ingrowth member'. Like the first tubular ingrowth member, it is preferred that the second tubular ingrowth member is radially spaced from the part of the connecting member around which it extends so that an annular dermal ingrowth space is provided. In a most preferred embodiment, the connecting and second tubular members are coaxial cylinders. This arrangement allows the dermis to infiltrate the ingrowth member and form a seal against the outer wall of the connecting member. Thus, this part of the connecting member provides a barrier against which the dermis will grow. It will prevent ingrowth of the dermis into the serosal tissue of the bowel segment, which provides a barrier to the possible infection path from the epidermis to the bowel segment. In addition, and perhaps more importantly, the secure bond that is enabled prevents downgrowth of epidermis along the cylinder. The second tubular ingrowth member preferably comprises a mesh that is differently configured (e.g. finer) than mesh used elsewhere, i.e. it may be optimized for dermal ingrowth.

The provision of a dermal mesh spaced from the body of an implant represents another inventive concept and so, viewed from a further aspect, there is provided a percutaneous ostomy implant for implantation into the abdominal wall of a patient, the implant comprising: a connecting member for mounting an external detachable device thereto; a tubular ingrowth member arranged around the connecting member, wherein the tubular ingrowth member is adapted to abut dermal tissue in use such that the dermal tissue may infiltrate the tubular ingrowth member and form a seal against the adjacent part of the connecting member, thereby securing and sealing the implant to the dermis. The implant may have any of the other preferred features described herein.

In particular, it is preferred that there is a radial gap between the connecting member and the tubular ingrowth member, such that a preferably annular dermal ingrowth space may be provided.

Although the provision of an ingrowth member specifically for the dermis provides good security and sealing, it is preferred that the implant further comprises a radially-extending dermal anchor to engage the abdominal wall beneath the dermis, preferably just beneath the dermis, e.g. in the junction between dermis and the underlying fatty tissue. It will be appreciated that this anchor is provided far higher up the implant (i.e. towards the exposed end in use) than the known anchors that are intended to engage with fatty tissue or muscle. As such, first and/or second tubular ingrowth members extend axially in both directions from the dermal anchor. Given the usual requirement for the connecting member to project above the skin's surface and for the implant to extend down to fat or muscle layers, typically, the dermal anchor will be located in the middle-third of the axial length of the implant. The dermal ingrowth member will usually be located immediately or closely above the dermal mesh.

A dermal anchor is any structure that extends radially from the implant in order to secure the implant in the axial direction relative to the dermis. Thus, it may comprise a flange or series of projections lying generally in an imaginary annulus surrounding the implant. The dermal anchor is preferably resilient and preferably also allows the ingrowth of tissue through and/or around it. A particularly preferred configuration comprises a series of C-shaped projections arranged circumferentially about the implant. Alternatively, the dermal anchor may comprise radially-extending ingrowth mesh, which may be metallic, as previously described, or polymeric, e.g. polypropylene. It may be rigid or flexible.

The provision of a dermal anchor represents a further inventive concept and so, viewed from another aspect, the invention provides a percutaneous ostomy implant for implantation into the abdominal wall of a patient, the implant comprising: a connecting member for mounting an external detachable device thereto, the implant being adapted to receive a bowel segment within it to form a stoma, wherein the implant further comprises a radially-extending dermal anchor to engage the abdominal wall beneath and substantially adjacent to the dermis.

The dermal anchor may have any of the forms discussed above. Its function is to reduce relative movement between the dermis and the implant—both lateral and vertical—and to distribute stresses over a wide area.

Preferably, an ingrowth member is provided in both axial directions from the dermal anchor, i.e. inwardly and outwardly.

The implant of this aspect preferably further comprises one or more ingrowth member(s) depending from the connecting member part. Preferably such an ingrowth member is adapted to receive the bowel segment within it to form a stoma so that serosal tissue of that bowel segment may infiltrate the ingrowth member. The implant may comprise an ingrowth member adapted to abut dermal tissue such that the dermal tissue may infiltrate at least a part of the ingrowth member, thereby securing and sealing the ostomy implant to the dermis. Most preferably, the implant comprises both such ingrowth members, i.e. an inner and an outer ingrowth member. The cylindrical ingrowth member(s) preferably extend axially in both directions from the dermal anchor.

As noted above, most conveniently, the dermal anchor extends radially from the outer tubular ingrowth member. It is possible for the outer tubular ingrowth member to extend axially only from the connecting member to the dermal anchor (indeed it may entirely overlie the connecting member), so that the dermal anchor is located at the bottom of the ingrowth member. However, more preferably, the outer tubular ingrowth member comprises a first portion above the dermal anchor for ingrowth of dermis and a second portion below the dermal anchor for ingrowth of sub-dermal tissue (including any relevant tissue layer beneath the dermis, such as fatty tissue, muscle or fascia). As noted above, the first portion may have differently configured, e.g. finer, mesh than the second. This additional layer of ingrowth material provides for a larger ingrowth area for sub-dermal and serosal tissue and hence results in a more secure implant.

This may in itself be sufficient to secure the implant in place. However, it is most preferred for the implant to further comprise an anchoring flange for securing the implant in sub-dermal tissue, particularly in fat or muscle, or adjacent the fascia. This may be located at the lower end of the outer tubular ingrowth member. As is known from the applicant's prior patent applications, the anchoring flange is preferably circular and penetrated by multiple small holes to allow ingrowth of connective tissue. It preferably comprises an axially resilient structure, e.g. formed from inner and outer concentric rings, the inner ring being attached to one end of the cylindrical mesh and the outer ring being connected to the inner ring by a plurality of S-shaped connecting members.

In the case of a double mesh structure, the inner tubular ingrowth member may conveniently terminate in a coplanar manner with the anchoring flange and be radially inwardly spaced therefrom. However, an alternative is for the inner tubular ingrowth member to extend axially below the outer tubular ingrowth member, e.g., the inner tubular ingrowth member may extend axially below the anchoring flange. This provides still greater security for the implant and specifically for the bowel segment inside the inner mesh. When this is done, it is preferred for the lower part of the inner tubular member to be generally trumpet-shaped, frusto-conical or funnel-shaped such that its lower end has a greater diameter than its upper end. This is to prevent possible trauma to the bowel segment by shearing forces imposed by the end of the tubular member and also to provide more space for the mesentery.

This represents a still further inventive concept and so, viewed from another aspect, there is provided an ostomy implant comprising a tubular ingrowth member which, in use surrounds a bowel section, wherein the lower part of the tubular member is generally trumpet-shaped, frusto-conical or funnel-shaped such that its lower end has a greater diameter than its upper end.

The inventors have recognized that the dermal anchor may be applied to other types of implant and so, viewed from a further aspect, the invention provides a percutaneous implant comprising an implant body and a radially-extending dermal anchor to engage the abdominal wall beneath and substantially adjacent to the dermis. The dermal anchor is preferably as described above.

Likewise, the dermal mesh may also be applied to other types of implant and so viewed from a still further aspect there is provided a percutaneous implant comprising an implant body and a tubular ingrowth member arranged around the implant body wherein the tubular member is adapted to abut dermal tissue in use such that the dermal tissue may infiltrate the tubular ingrowth member and form a seal against the adjacent part of the implant body, thereby securing and sealing the implant to the dermis. The dermal mesh is preferably as describe above. In particular it is preferably arranged around and spaced from the implant body as in relation to the connecting member.

In either case, the implant may be an ostomy implant as previously described, but it may be any other sort of percutaneous implant, for example an implant to provide a catheter insertion port. Thus, the implant body may comprise a tissue-impermeable portion surrounding a void, which may form a passage through the implant. The implant may comprise one or more ingrowth members (the dermal mesh may, when appropriate, form part of one of these), for example as described previously and the dermal mesh and dermal anchor may be combined in a single implant. The invention also extends to a method comprising providing such an implant and implanting it in the body of a patient.

It will be appreciated that the present invention also extends to a method of performing an ostomy comprising the use of an implant as described above. Thus, according to a further aspect there is provided a method of performing an ostomy comprising providing an ostomy implant according to any aspect or any preferred form thereof as described above; providing a suitable opening for the implant in the body of a patient; implanting the implant in the opening and drawing a bowel segment into the implant to provide a stoma. The method is most preferably as described in more detail below.

The ostomy implant of the invention allows a continent ostomy to be provided because the natural resilience of the vessel tissue (which is constricted to some extent where it is drawn into the implant) occludes the aperture through the implant and results in a valve being formed. Provided that a reservoir is formed so that fluid pressure is restricted, the valve enables the ostomy to be continent. It may be drained using a catheter in the known manner, or some other evacuation system may be used. A lid is preferably provided to provide further protection against leakage and to protect the exposed vessel.

Thus, viewed from a further aspect the invention provides a method of performing a continent ostomy comprising: implanting a percutaneous ostomy implant according to any aspect or any preferred form thereof as described above in the abdomen; drawing a section of vessel (e.g. bowel) into the implant; and securing it to form a stoma; wherein the internal diameter of the implant is selected to constrict the vessel such that the natural resilience of the vessel tissue resiliently occludes the stoma, thereby forming a valve. The implant and/or method are preferably as set out herein.

This aspect of the invention also extends to an ostomy implant dimensioned to form a continent ostomy by means of the above method and to a method of manufacturing such an implant which comprises the step of dimensioning the implant for a given patient or class of patients such that a valve will be formed when the implant is used in such method. Again, the method of manufacture is preferably as set out herein. The implant is preferably used or provided in combination with a lid to prevent leakage and/or to protect the stoma. However, it may also be used in combination with a bag or an evacuation device. Thus, viewed from a still further aspect the invention provides an ostomy implant according to any aspect or preferred from described herein, in combination with a mating lid, bag or evacuation device. Mating is typically by means of a part of the lid, bag or evacuation device having a part that in use engages with the connecting member of the implant and preferably connects thereto by means of an engagement means, such as a circumferential groove, around the circumference of the connecting member of the implant. However, it is possible for engagement to be wholly or partially with an internal surface of the connecting member.

BRIEF DESCRIPTION OF THE DRAWINGS

Embodiments of the invention will now be described, by way of example only, and with reference to the accompanying drawings.

DETAILED DESCRIPTION OF THE INVENTION

In the following discussion, terms such as "above", "beneath" etc. refer to the orientation of the implants and other components as shown in the relevant figures, so that the part of the implant which in use projects from a patient's body is regarded as the top of the implant.

Figure 1:
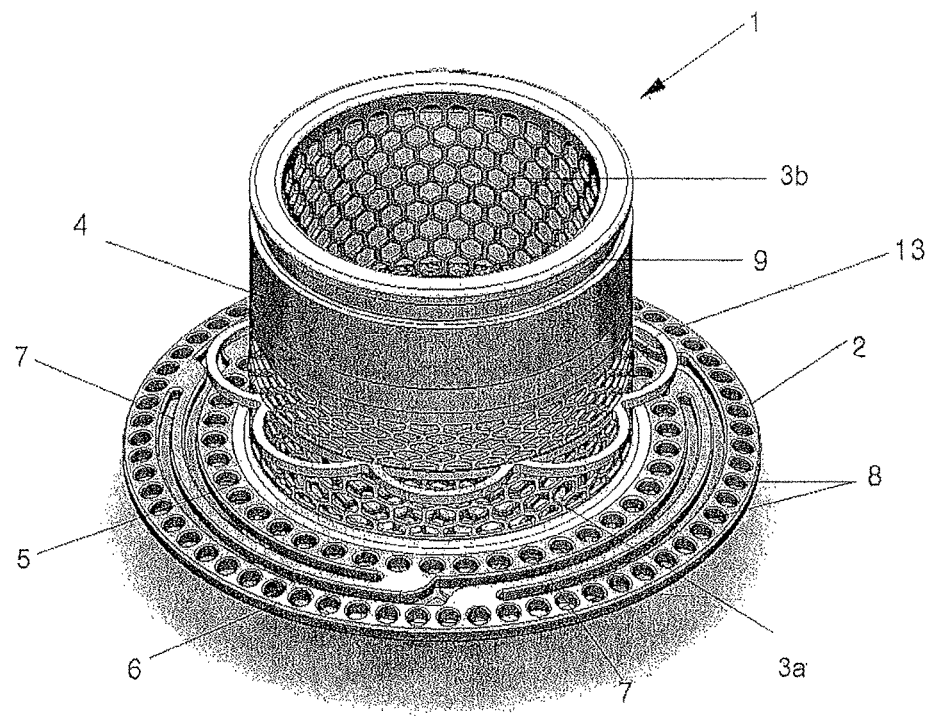
FIG. 1 is a perspective view from above of an implant according to a first embodiment of the invention.
Figure 2:
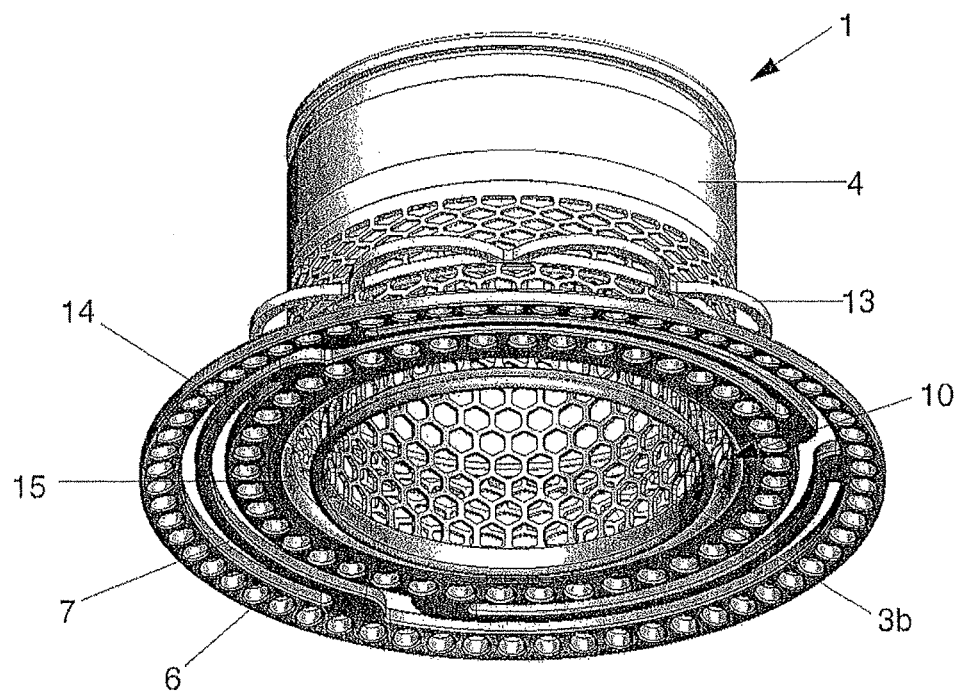
FIG. 2 is a perspective view from below of the implant of FIG. 1.
Figure 3:
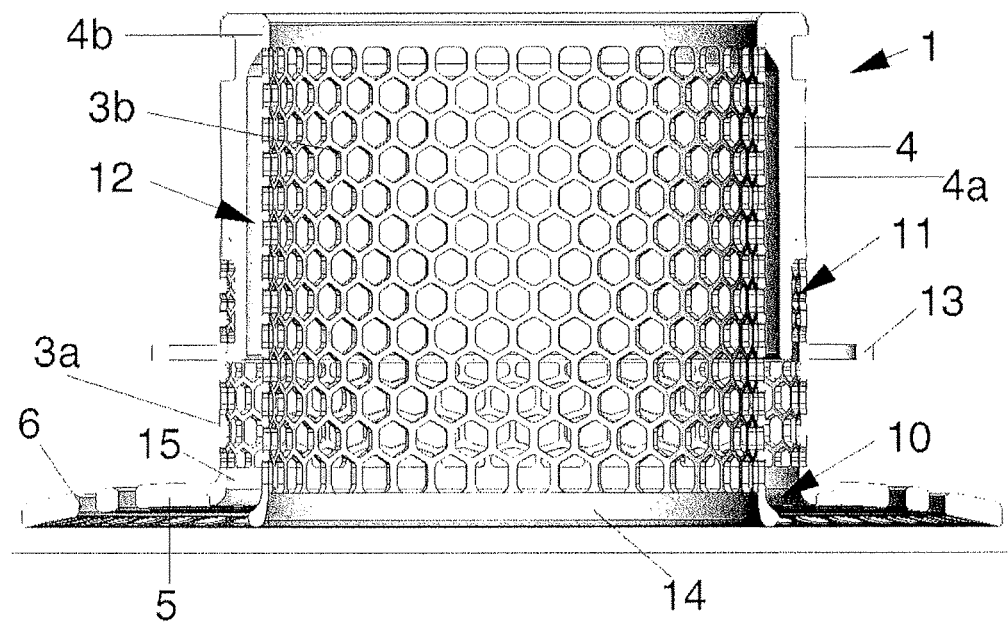
FIG. 3 is a cross-sectional view of the implant of FIG. 1.

With reference to FIGS. 1 to 3, a first embodiment 1 of an implant according to the invention comprises four components: a circular anchoring flange 2, an outer mesh cylinder 3a, an inner mesh cylinder 3b and a cylindrical end part 4. These components are each formed separately from machined titanium, with the mesh cylinders 3a, 3b being formed by laser cutting. The individual components are then laser-welded together.

The end part 4 is in the form of a connection ring. It has a circumferential groove 9 on its outer surface to allow for the connection of detachable devices such as lids, bags, etc. The outer mesh cylinder 3a is attached to the outer surface of the end part 4 and the inner mesh cylinder is attached to its inner surface. Both mesh cylinders 3a, 3b depend downwardly (as shown) from end part 4, with the anchoring flange 2 being attached to a termination ring 15 at the lowermost end of the outer cylinder 3a.

With reference to FIG. 3, it will be noted that the outer mesh cylinder 3a depends from a radially outwardly projecting part 4a of the end part 4 such that it is spaced radially from the lower part thereof to leave an annular tissue ingrowth space 11. Likewise, the inner mesh cylinder 3b depends from a radially inwardly projecting part 4b of the end part 4 to provide a further annular tissue ingrowth space 12.

The anchoring flange 2, best seen in FIGS. 1 and 2, is as described in the applicant's earlier patent applications referred to in the introduction. It has concentric inner and outer rings 5, 6 connected by S-shaped members 7 to form an axially resilient structure. A multitude of holes 8 are provided to allow ingrowth of tissue through the rings. Only the inner ring 5 of the anchoring flange 2 is connected to termination ring 15 at the end of the outer cylindrical mesh 3a so that the resilient structure allows a degree of play between the outer mesh cylinder 3a and the outer ring 6 of the anchoring flange. There is no connection to the inner cylindrical mesh 3b. As may be seen from FIGS. 2 and 3, its lower end is provided with a termination ring 14 which spaced inwardly from, and is generally coplanar with, the anchoring flange. As such, an annular gap 10 is provided between the anchoring flange 2 and the inner mesh cylinder 3b.

In addition to the anchoring flange 2, which is intended for engagement with fat layers (or muscle, or muscle and fat layer) in the abdominal wall of a patient, this embodiment is additionally provided with dermal anchor 13. This is mounted to the outside of the outer mesh cylinder 3b. It comprises a series of C-shaped radial projections arranged around the mesh surface. It will also be noted that outer mesh cylinder 3b has a finer mesh size above the dermal anchor 13 than below it. This finer mesh is designed to facilitate optimum ingrowth of the dermis. The mesh below the dermal anchor 13, i.e. the sub-dermal mesh, extends at least 6 mm in the axial direction to provide a barrier against any infection spreading down subdermally.

Figure 4:
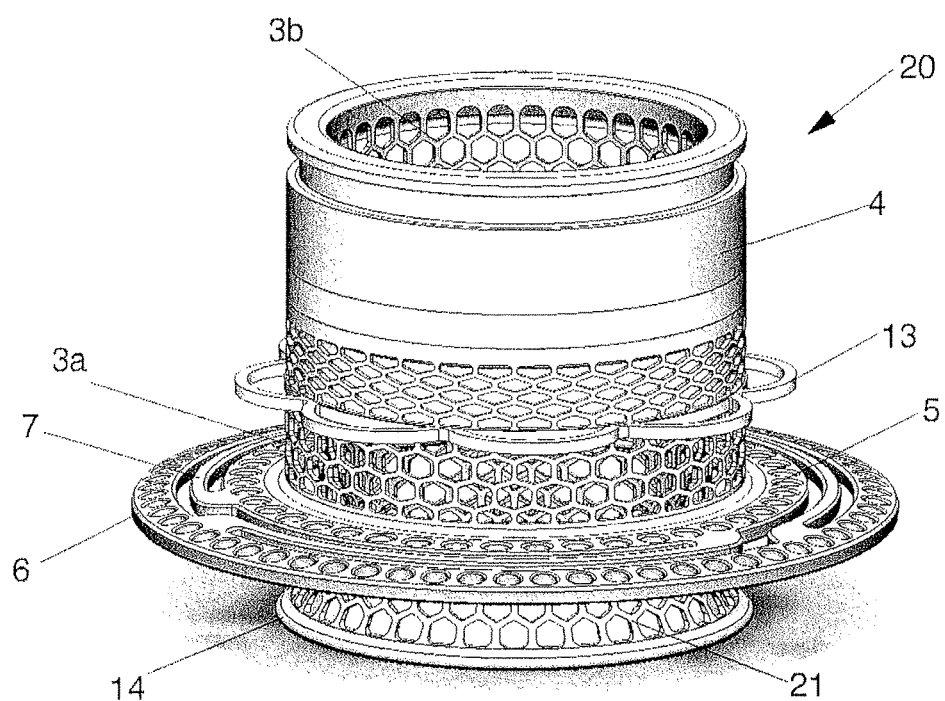
FIG. 4 is a perspective view from above of an implant according to a second embodiment of the invention.
Figure 5:
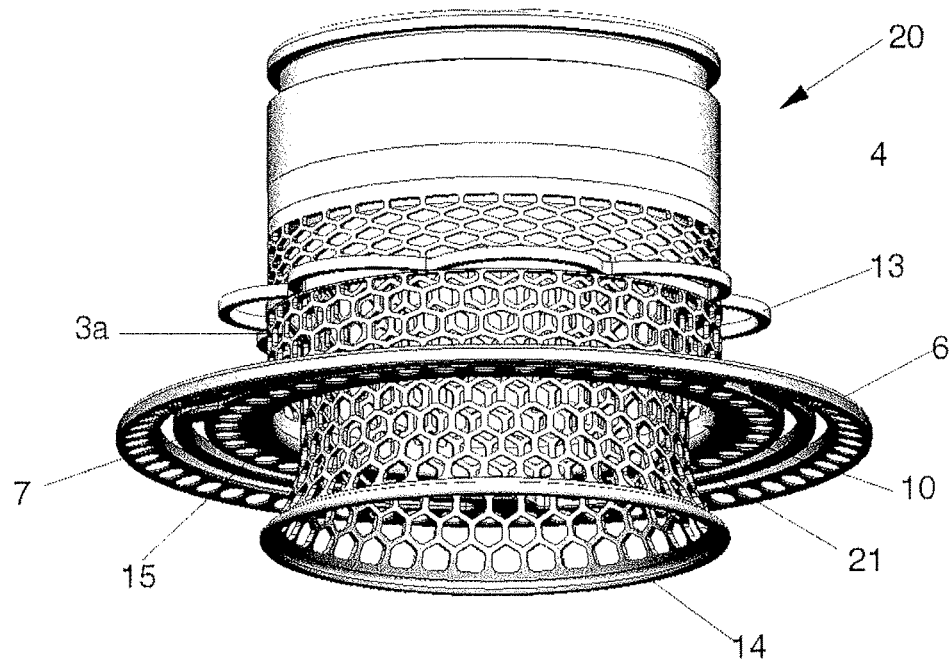
FIG. 5 is a perspective view from below of the implant of FIG. 4.
Figure 6:
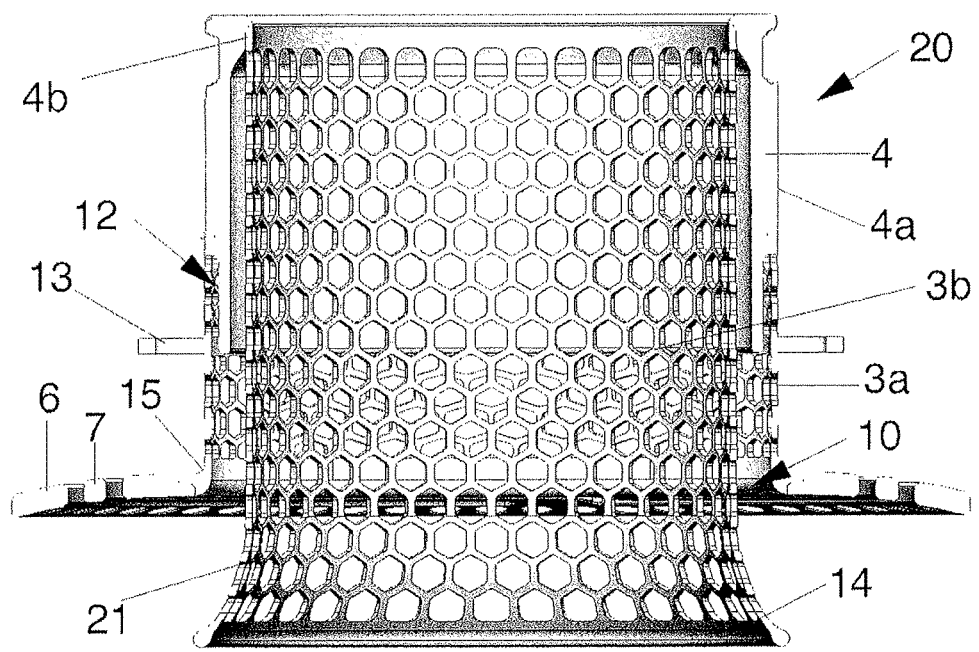
FIG. 6 is a cross-sectional view of the implant of FIG. 4.

A second embodiment of the invention 20 is shown in FIGS. 4 to 6. Features corresponding to those in the first embodiment are identified by the same reference numbers and, insofar as they are identical, they will not be described further. The second embodiment differs from the first embodiment in that its inner mesh cylinder 3a is elongated. As may most clearly be seen from FIGS. 5 and 6, it extends through the centre of the anchoring flange 2 into a trumpet-shaped lower portion 21. This has a termination ring 14 with a diameter similar to that of the outer mesh 3a which is above it.

Figure 7:
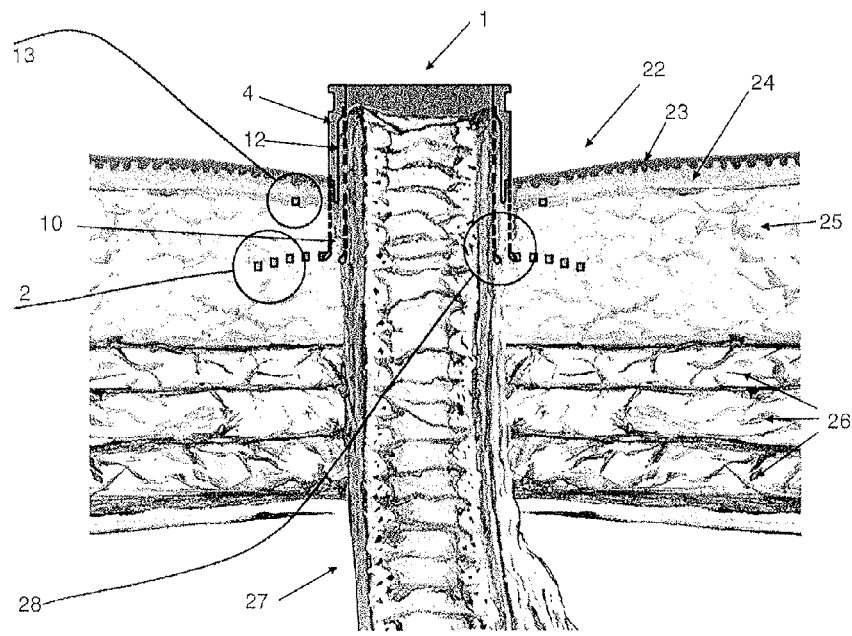
FIG. 7 is a cross-sectional view of the implant of FIG. 1 implanted in the abdominal wall of a patient.
Figure 8:
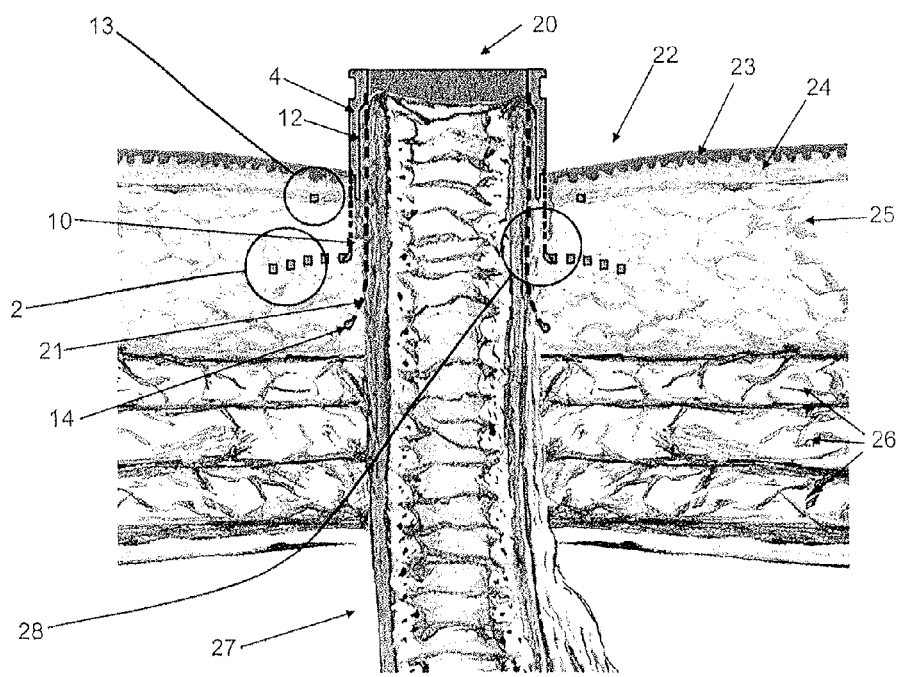
FIG. 8; is a cross-sectional view of the implant of FIG. 4 implanted in the abdominal wall of a patient.

FIGS. 7 and 8 show the first and second embodiments 1, 20 of the invention respectively implanted into the abdominal wall 22 of a patient after healing and ingrowth of tissue has taken place. As shown in those figures, the abdominal wall comprises the epidermis 23 and dermis 24, fat layer 25 and muscle layers 26.

The implant 1, 20 has been implanted in a generally cylindrical opening formed in the abdominal wall formed in a manner that will be discussed in more detail below. The anchoring flange 3 is located in an annular incision within the fat layer 25 and the dermal flange 13 is located in a further annular incision just beneath the dermis 24. The ileum has been drawn up inside inner mesh cylinder 3b.

The dermal flange is designed to be located in the junction between dermis and the underlying fatty tissue (about 5-8 mm beneath the surface of the skin). It ensures that the implant remains in the correct position in relation to the dermis so that the dermis abuts the upper portion of the outer mesh cylinder 3a. This prevents skin downgrowth and enables it to grow through the fine mesh and into ingrowth space 12 so that it comes into contact with the lower part of the end portion 4. Thus, the end portion 4 is sealed against the skin to provide an infection barrier and to prevent a possible leakage path in the event that the ileum recedes within the implant. The dermal anchor 13 assists in maintaining this condition. The purpose of the dermal anchor is also to reduce the lateral stresses posed on the outer mesh ingrowth area.

Beneath the dermal anchor 13, as in the applicant's earlier patent applications, the provision of mesh surfaces enables ingrowth of tissue into, around and through the implant. Thus, fatty tissue grows through both mesh cylinders 3a and 3b and up into ingrowth space 12. Likewise, serosal tissue on the outer surface of the ileum grows through ingrowth mesh 3b into the space between it and ingrowth mesh 3a and into ingrowth space 12. In this way the serosal and fatty tissues grow together. The result is a very stable ingrowth zone where sub-dermal and ileum tissue meet at the lower end of cylindrical end part 4. This provides a safe and fluid-tight sealing function.

The fatty tissue also grows through the openings and holes 8 in the anchoring flange 2 in the known manner. This ingrowth provides for secure attachment between the abdominal wall and the ileum and also holds the implant securely in place.

The provision of a double-mesh structure allows for more extensive ingrowth and hence more secure attachment than the prior single mesh implants. However, it also provides a significant advantage in terms of reducing the risk of infection. This is because, except at the top of the end part 4, these components are not contiguous and so there is no infection path between the outer mesh 3a, and inner mesh 3b, which is in contact with the ileum. This is important because the outer mesh 3a extends through the epidermis and is therefore exposed to possible sources of infection. This arrangement means that there is no direct infection path from the skin to the ileum. Also the stresses on the tissue (ingrowth area/sealing area) between the meshes are reduced and is "spread out"/distributed in a advantageous manner due to the surrounding mesh structures.

The extended portion 21 of the inner mesh 3b provided in the second embodiment (FIG. 8) enables a longer portion of the ileum to be encircled by the implant. This enables a greater degree of tissue ingrowth into the implant. Its trumpet shape results in its termination ring being radially displaced from the ileum, which reduces the risk of shearing or tearing trauma being caused to the ileum by the end of the inner mesh and also to provide more space for the mesentery.

After the implant has healed it is used in essentially the same manner as those described in the applicant's prior patent applications. Thus, the connecting ring formed by the end portion 4 may be used for the mounting of a suitable bag. Alternatively, as is also known, because the resilient tissue that forms the bowel is constricted as it passes through the implant to form a valve, the implant may be used to provide a continent system. Over a period of time, the section of bowel adjacent the implant will tend to enlarge so that a reservoir or "pouch" is formed, or a reservoir can be constructed at implantation of the implant or an "old" reservoir can be used. The stoma may be emptied at intervals using a catheter. A removable lid (not shown) may additionally be provided to prevent leakage and to protect the stoma. In this case there is no need for a bag.

The implant is implanted into the patient in a similar manner to that described in the applicant's earlier patent applications WO 2007/099500, WO 2009/024568 and WO 2010/000851, although those techniques are modified to some extent in view of the improvements provided by the invention.

Figure 9:
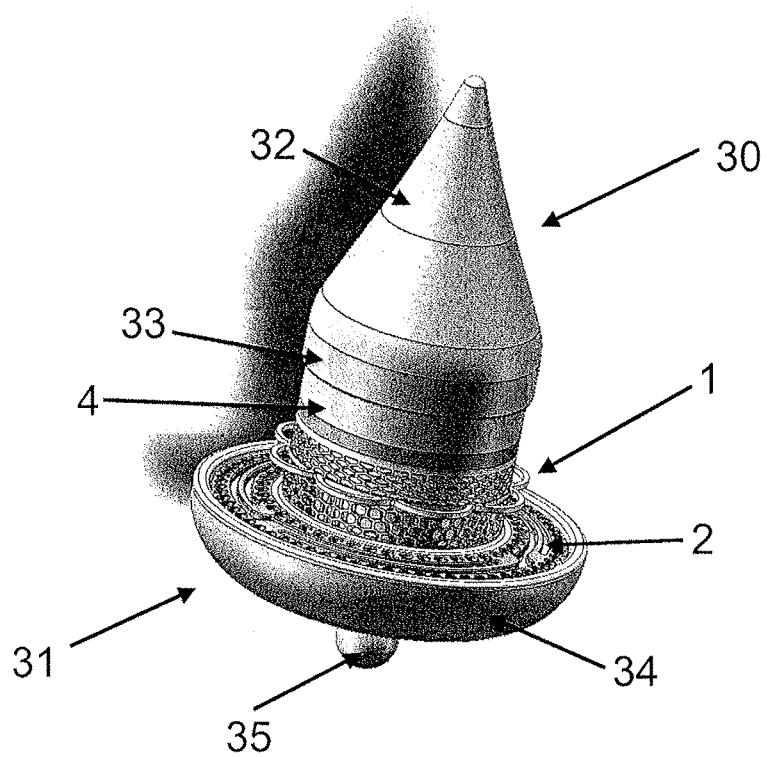
FIG. 9 is a perspective view of the implant of FIG. 1 connected to a two-part insertion instrument for positioning the implant in the abdominal wall.
Figure 10:
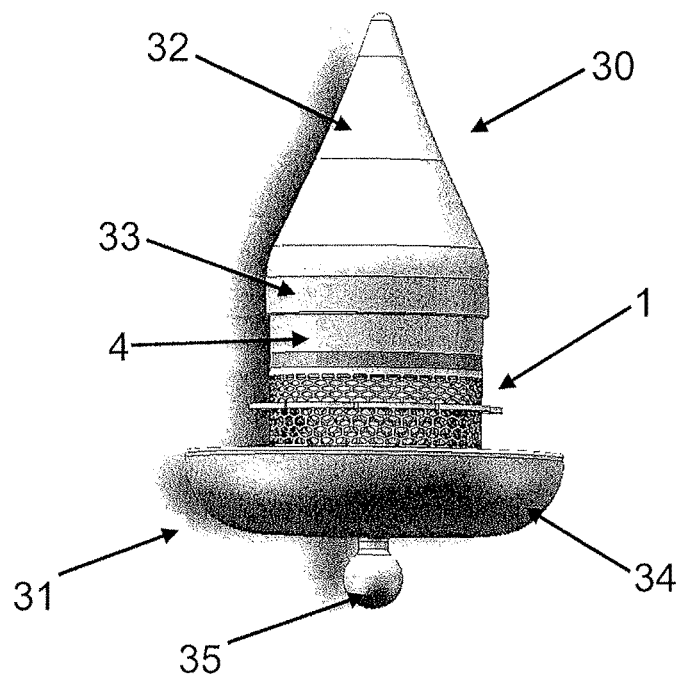
FIG. 10 is an elevation corresponding to FIG. 9.

As shown in FIGS. 9 and 10, a specially designed two-part insertion instrument 30 31, is used for facilitated positioning of the implant 1, 20 in the abdominal wall 22. This is a development of a tool disclosed in WO 2010/000851. The first part 30 has a conical upper part 32 and a lower cylindrical part 33. The latter fits snugly around the end portion 4 of the implant 1, 20 and the former is designed to be pushed through a resilient opening in the abdominal wall. The second part 31 has a bowl-shaped body 34 and a handle 35. The body 34 is configured to fit around the anchoring flange 2.

Prior to implanting the implant 1, 20, the two parts of the instrument 30, 31 are fitted around the respective ends of the implant. The implant may then be inserted through the abdominal wall, with the conical upper 30 part facilitating insertion, whilst it is manipulated using handle 35. Once the implant is in place, the parts of the instrument may then be withdrawn.

Figure 11:
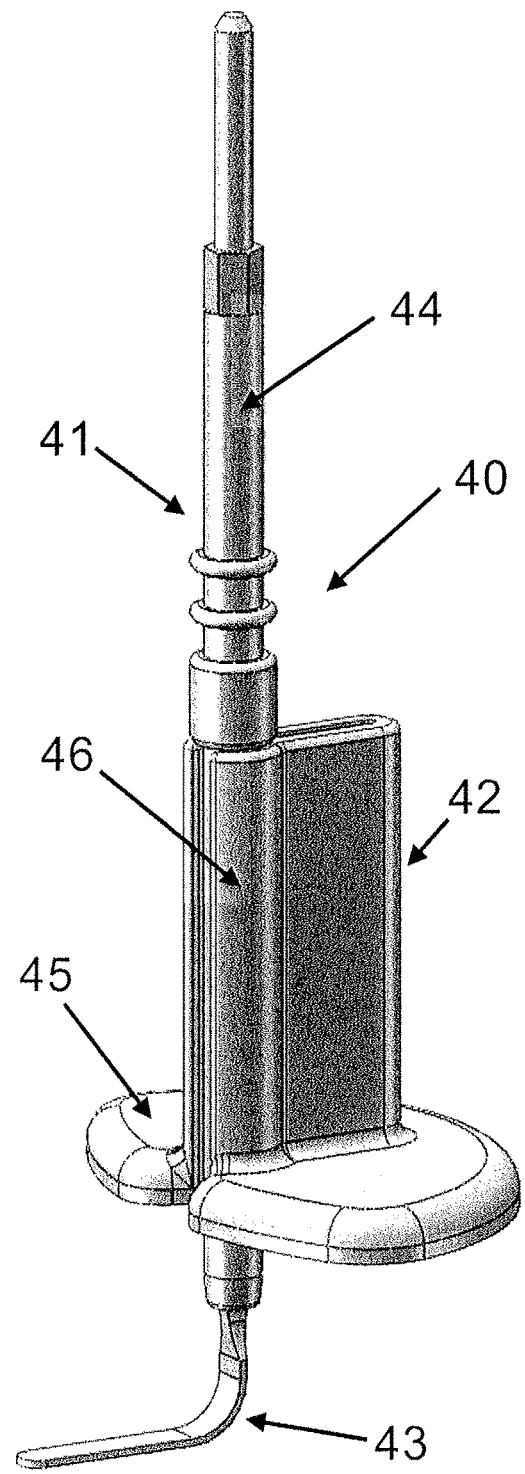
FIG. 11 is a perspective view of a diathermy tool used in connection with the embodiments.
Figure 12:
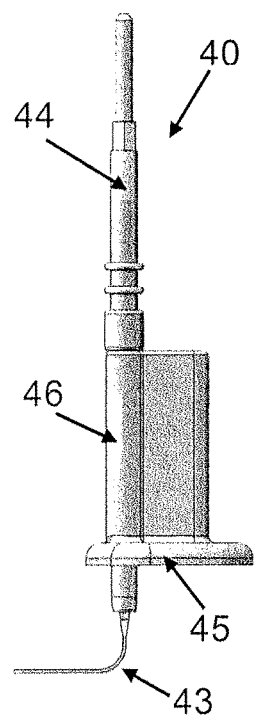
FIG. 12 an elevation of the diathermy tool of FIG. 11.
Figure 13:
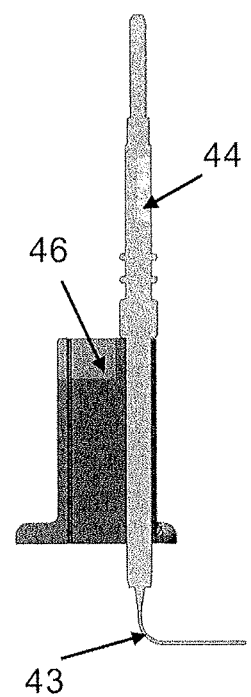
FIG. 13 is a sectional view of the diathermy tool of FIG. 11.

It will be appreciated that it is important that the implant is correctly located in the axial direction so that the dermal flange is correctly located beneath the dermis. Consequently, the annular incision for the anchoring flange must be the correct depth below the skin's surface. FIGS. 11, 12 and 13 show a specialist diathermy tool to assist in forming a suitable annular incision.

The tool 40 comprises a conventional diathermy tool 41 in combination with a snap-fit handle 42 and modified cutter 43. The tool 42 has a handle 44 at the upper end as shown and is arranged to receive a single-use cutter 43 at its lower end. The cutter 43 is modified in that it is bent into an L-shape by means of a suitable jig. This has been found not to adversely affect operation of the cutter.

Snap-fit handle 42 fits around the tool handle 44 and snaps into place. It has a main body 46 which is formed integrally with locating flange 45. This extends in a plane which is perpendicular to the tool handle axis and hence parallel to the end of the L-shaped cutter 43. Thus, if the flange 45 is placed on and moved over a surface, the cutter will move in a plane parallel to, and a fixed distance below, that surface. In the context of the present invention, that surface is the skin of a patient and so the tool may be used to cut an incision for the anchoring flange of an implant at the correct depth. To achieve this, the cutter 43 is inserted into an incision and the tool is then moved around the circumference of the incision with the cutter oriented in a radially-outward direction.

The procedure for implanting the embodiments of the invention will now be described.

The first step is to prepare the patient to receive the implant. To do this, a suitable abdominal incision, e.g., a midline 100-120 mm abdominal incision, is made. Next, the bowel is prepared in order to make a stoma is according to standard procedures. When this has been done, the size of intestine and abdominal wall are checked and a suitable height and diameter implant is selected. The bowel segment is then inserted into a dummy implant of the selected diameter to make sure there is enough room for a catheter to pass through the implant and that the entry is atraumatic.

The second step is the preparation for the placement of the port. By atraumatic dissection from the midline a pocket is created above the external fascia so that the space is sufficient to place the Port. The location of the stoma is marked on the abdominal wall preoperatively. A small circular hole is then made in the skin where the stoma/implant should be placed. Next, a passageway through the subcutis is made by blunt dissection and then, using the diathermy tool describe above, a cleavage is made in the subcutaneous layer for the anchoring flange 2. Electrocautery or a scalpel is used to make a cleavage in the dermis/subcutis junction for the dermal anchor.

Step three is the placement of the implant. Firstly, the implant is fitted to the insertion instrument 30, 31. Next the assembly is inserted into the pocket above the fascia. It is pushed through the subcutis and the cone is driven against the hole in the skin. The opening in the skin is customized by cutting against the cone while pressing the Port-Inserter assembly against the opening. The aperture should be circular and not too large, so that he skin will tighten well to the cylinder top, but without risk of necrosis. The insertion instrument is then withdrawn and the anchoring flange is located in the cleavage previously created in the subcutaneous layer. A check is then made that the port is not inclined and that the skin fits tightly around the implant. If necessary sutures may be used to ensure that the skin fits tightly around the implant.

Step four is to create the stoma. This is done by making a channel for the stoma through the muscle layer and peritoneal membrane. The distal ileum segment is then inserted through the abdominal wall and the implant. The efferent bowel end is everted (ad modum Turnbull) (10-20 mm) above the Port and the efferent everted distal end of the stoma is pulled down against the top of the Port. A check is then made to ensure that the intestine is in contact with the implant mesh and the space is filled with intestinal tissue before anchoring the intestine to the peritoneum with sutures.

The next step (step five) is to ensure passage. It is important to make sure there is enough room for faeces to pass through the implant. If not, the port should be replaced with one of a larger diameter. In addition, it is important that there is enough room for a catheter to pass through the implant and that the entry is atraumatic. Again, if this is not possible, a larger port is required.

Finally, step six is to close the abdomen according to the normal procedure.

After implantation, a catheter is used to drain the pouch whilst healing and tissue ingrowth takes place. As this occurs, the serosal tissue of the ileum grows through the mesh layers of the implant into contiguity with the fatty tissue of the abdominal wall and the dermis spreads through outer mesh 3a into ingrowth space 12. Any protruding part of the ileum may then be removed and, after a suitable further interval, the catheter may be withdrawn leaving a continent ostomy. A lid (or bag, or other evacuation system) may then be fitted onto end part 4 by means of circumferential groove 9 in the known manner.

What is claimed is:

1. A percutaneous ostomy implant for implantation into the abdominal wall of a patient, the implant comprising (a) a first cylinder of a connecting member for mounting an external detachable device thereto and being configured and dimensioned to receive an intestine segment within it to form a stoma, wherein the implant further comprises (b) a second cylinder of the same diameter as the connecting member and that includes a tubular mesh structure and a radially-extending dermal anchor comprising a radially-extending first ingrowth mesh configured and positioned on the second cylinder to engage the abdominal wall beneath and substantially adjacent to the dermis structure to secure the implant in the axial direction relative to the dermis, wherein the tubular mesh structure further includes a second ingrowth mesh located above the dermal anchor for ingrowth of dermis and a third ingrowth mesh located below the dermal anchor for ingrowth of sub-dermal tissue, and (c) an inner fourth ingrowth mesh in the form of a cylindrical tube that is of smaller diameter than the connecting member and extends below the third ingrowth mesh, with the fourth ingrowth mesh attached to an inner portion of the connecting member and spaced from the second ingrowth mesh.

2. The percutaneous ostomy implant according to claim 1, wherein the second ingrowth mesh is attached to the connecting member at one end and to the dermal anchor at its opposite end.

3. The percutaneous ostomy implant according to claim 2, wherein the second ingrowth mesh has a finer mesh size than the third ingrowth mesh.

4. The percutaneous ostomy implant according to claim 3, wherein the implant has an axial length and the dermal anchor is located in a middle third portion of the axial length of the implant.

5. The percutaneous ostomy implant according to claim 1, wherein the second ingrowth mesh is attached to an outer portion of the connecting member and axially spaces the dermal anchor from the connecting member.

6. The percutaneous ostomy implant according to claim 1, further comprising an anchoring flange.

7. The percutaneous ostomy implant according to claim 6, wherein the anchoring flange comprises a circular, axially resilient structure that includes by multiple holes to allow ingrowth of connective tissue.

8. The percutaneous ostomy implant according to claim 1, wherein the dermal anchor is resilient and is metallic or a polymeric.

9. A percutaneous ostomy implant for implantation into the abdominal wall of a patient, the implant comprising (a) a first cylinder of a generally cylindrical connecting member for mounting an external detachable device thereto and being configured and dimensioned to receive an intestine segment within it to form a stoma, and (b) a second cylinder of the same diameter as the connecting member and that includes a tubular mesh structure and a radially-extending dermal anchor comprising a radially-extending first ingrowth mesh configured to facilitate tissue growth and positioned on the second cylinder to engage the abdominal wall beneath and substantially adjacent to the dermis structure to secure the implant in the axial direction relative to the dermis, wherein the tubular mesh structure includes a second ingrowth mesh located above the dermal anchor for ingrowth of sub-dermal tissue, a third ingrowth mesh located below the dermal anchor for ingrowth of sub-dermal tissue, and an inner fourth ingrowth mesh in the form of a cylindrical tube that is of smaller diameter than the connecting member and extends below the third ingrowth mesh, with the fourth ingrowth mesh attached to an inner portion of the connecting member and spaced from the second ingrowth mesh, wherein a lower portion of the implant further comprises (c) a termination ring having a frusto-conical shape with an outer diameter that is not larger than that of the dermal anchor.

10. The percutaneous ostomy implant according to claim 9, wherein the second ingrowth mesh is attached to the connecting member at one end and to the dermal anchor at its opposite end.

11. The percutaneous ostomy implant according to claim 9, wherein the second ingrowth mesh is attached to an outer portion of the connecting member and axially spaces the dermal anchor from the connecting member.

12. The percutaneous ostomy implant according to claim 9, further comprising an anchoring flange.

13. The percutaneous ostomy implant according to claim 12, wherein the anchoring flange comprises a circular, axially resilient structure that includes by multiple holes to allow ingrowth of connective tissue.

14. The percutaneous ostomy implant according to claim 9, wherein the dermal anchor is resilient and is metallic or a polymeric.

15. The percutaneous ostomy implant according to claim 9, wherein the second ingrowth mesh has a finer mesh size than the third ingrowth mesh.

16. A percutaneous ostomy implant for implantation into the abdominal wall of a patient, the implant comprising:

a first cylinder of a connecting member for mounting an external detachable device thereto and being configured and dimensioned to receive an intestine segment within it to form a stoma, a second cylinder of the same diameter as the connecting member that includes a radially-extending dermal anchor comprising a radially-extending first ingrowth mesh configured and positioned on the second cylinder to engage the abdominal wall beneath and substantially adjacent to the dermis structure to secure the implant in the axial direction relative to the dermis, and a tubular mesh structure that includes a second ingrowth mesh located above the dermal anchor for ingrowth of sub-dermal tissue and a third ingrowth mesh located below the dermal anchor for ingrowth of sub-dermal tissue, and an inner fourth ingrowth mesh in the form of a cylindrical tube that is of smaller diameter than the connecting member and extends below the third ingrowth mesh, with the fourth ingrowth mesh attached to an inner portion of the connecting member and spaced from the second ingrowth mesh;

wherein the second ingrowth mesh is attached to an outer portion of the connecting member and axially spaces the dermal anchor from the connecting member.

17. The percutaneous ostomy implant according to claim 16, wherein the second ingrowth mesh has a finer mesh size than the third ingrowth mesh.

18. The percutaneous ostomy implant according to claim 16, wherein the second ingrowth mesh is tubular and is attached to the connecting member at one end and to the dermal anchor at its opposite end.

19. The percutaneous ostomy implant according to claim 16, wherein the second ingrowth mesh is tubular and configured and dimensioned to abut dermal tissue to allow the dermal tissue to infiltrate at least a part of the second ingrowth mesh, thereby securing and sealing the ostomy implant to the dermis.

20. The percutaneous ostomy implant according to claim 16, wherein the dermal anchor is resilient and is metallic or a polymeric.

* * * * *